(12) United States Patent
Nguyen et al.

(10) Patent No.: US 12,349,982 B2
(45) Date of Patent: Jul. 8, 2025

(54) INSTRUMENT BOURNE OPTICAL TIME OF FLIGHT KINEMATIC POSITION SENSING SYSTEM FOR PRECISION TARGETING AND METHODS OF SURGERY

(71) Applicant: Surgical Targeted Solutions Inc., Akron, OH (US)

(72) Inventors: Quang-Viet Nguyen, Aldie, VA (US); Ian P. Kay, Fairlawn, OH (US); David B. Kay, Akron, OH (US); Bryan Den Hartog, St. Paul, MN (US); Richard Frank, Newtonville, MA (US)

(73) Assignee: Surgical Targeted Solutions Inc., Akron, OH (US)

( * ) Notice: Subject to any disclaimer, the term of this patent is extended or adjusted under 35 U.S.C. 154(b) by 866 days.

(21) Appl. No.: 17/428,040

(22) PCT Filed: Feb. 20, 2020

(86) PCT No.: PCT/US2020/019022
§ 371 (c)(1),
(2) Date: Aug. 3, 2021

(87) PCT Pub. No.: WO2020/172397
PCT Pub. Date: Aug. 27, 2020

(65) Prior Publication Data
US 2022/0142711 A1 May 12, 2022

Related U.S. Application Data

(60) Provisional application No. 62/808,495, filed on Feb. 21, 2019.

(51) Int. Cl.
*A61B 34/20* (2016.01)
*A61B 17/16* (2006.01)
(Continued)

(52) U.S. Cl.
CPC .......... *A61B 34/20* (2016.02); *A61B 17/1622* (2013.01); *A61B 17/1703* (2013.01);
(Continued)

(58) Field of Classification Search
CPC . A61B 34/20; A61B 17/1622; A61B 17/1703; A61B 34/37; A61B 34/74;
(Continued)

(56) References Cited

U.S. PATENT DOCUMENTS

| | | |
|---|---|---|
| 3,508,552 A | 4/1970 | Hainault |
| 5,020,088 A | 5/1991 | Tobin |

(Continued)

FOREIGN PATENT DOCUMENTS

| | | |
|---|---|---|
| CA | 2570336 C | 1/2013 |
| CN | 104271046 A | 1/2015 |

(Continued)

OTHER PUBLICATIONS

Keyence Corporation of America, Handheld Probe Coordinate Measuring Machine HM-5000, brochure, date unknown, pp. 1-36, Keyence Corporation of America, Itasca, IL.
(Continued)

*Primary Examiner* — Anne M Kozak
*Assistant Examiner* — Kaitlyn E Sebastian
(74) *Attorney, Agent, or Firm* — Farber LLC

(57) ABSTRACT

A medical devices en-vivo positional determination system using a plurality of optical time of flight (TDF) transceivers along with gyroscopic angular and mechanical distance sensors for the determination of absolute linear and angular positional information of the tool bit tip for the purposes of more accurate hand-held drilling or cutting, on the workpiece using forward kinematic equations calculated on a (Continued)

microcomputer to provide a real-time display of the 3-linear position and 2-angular orientation of the tool bit (such as a drill, scalpel, or wire driver).

16 Claims, 10 Drawing Sheets

(51) Int. Cl.
```
A61B 17/17      (2006.01)
A61B 34/00      (2016.01)
A61B 34/37      (2016.01)
A61B 90/00      (2016.01)
G01S 7/4865     (2020.01)
G01S 17/10      (2020.01)
G16H 40/63      (2018.01)
A61B 17/00      (2006.01)
A61B 34/10      (2016.01)
```
(52) U.S. Cl.
CPC .............. *A61B 34/37* (2016.02); *A61B 34/74* (2016.02); *A61B 90/37* (2016.02); *G01S 7/4865* (2013.01); *G01S 17/10* (2013.01); *G16H 40/63* (2018.01); *A61B 2017/00221* (2013.01); *A61B 2017/00725* (2013.01); *A61B 2034/107* (2016.02); *A61B 2034/2048* (2016.02); *A61B 2034/2057* (2016.02); *A61B 2034/2063* (2016.02); *A61B 2090/376* (2016.02)

(58) Field of Classification Search
CPC .......... A61B 90/37; A61B 2017/00221; A61B 2017/00725; A61B 2034/107; A61B 2034/2048; A61B 2034/2057; A61B 2034/2063; A61B 2090/376; A61B 2017/00734; A61B 90/39; A61B 2034/105; A61B 2034/2055; A61B 2034/2059; A61B 2090/365; A61B 2090/372; A61B 2090/3762; A61B 2090/3966; A61B 2090/502; A61B 34/10; A61B 2090/3937; A61B 90/10; A61B 34/30–77; A61B 5/06; G01S 7/4865; G01S 17/10; G16H 40/63
See application file for complete search history.

(56) References Cited

U.S. PATENT DOCUMENTS

| | | |
|---|---|---|
| 5,230,338 A | 7/1993 | Allen et al. |
| 5,230,623 A | 7/1993 | Guthrie et al. |
| 5,668,844 A | 9/1997 | Webber |
| 5,724,264 A | 3/1998 | Rosenberg et al. |
| 5,947,981 A | 9/1999 | Cosman |
| 5,957,934 A | 9/1999 | Rapoport |
| 5,980,526 A | 11/1999 | Johnson |
| 6,019,724 A | 2/2000 | Gronningsaeter et al. |
| 6,198,794 B1 | 3/2001 | Peshkin et al. |
| 6,285,902 B1 | 9/2001 | Kienzle et al. |
| 6,298,262 B1 | 10/2001 | Franck et al. |
| 6,520,969 B2 | 2/2003 | Lambrecht et al. |
| 6,711,432 B1 | 3/2004 | Krause et al. |
| 6,725,080 B2 | 4/2004 | Melkent et al. |
| 6,725,082 B2 | 4/2004 | Sati et al. |
| 6,785,571 B2 | 8/2004 | Glossop |
| 6,947,783 B2 | 9/2005 | Immerz |
| 6,980,849 B2 | 12/2005 | Sasso |
| 7,073,271 B2 | 7/2006 | Raab et al. |
| 7,217,276 B2 | 5/2007 | Henderson et al. |
| 7,237,556 B2 | 7/2007 | Smothers et al. |
| 7,302,288 B1 | 11/2007 | Schellenberg |
| 7,427,200 B2 | 9/2008 | Noble et al. |
| 7,447,565 B2 | 11/2008 | Cerwin |
| 7,458,977 B2 | 12/2008 | McGinley et al. |
| 7,477,926 B2 | 1/2009 | McCombs |
| 7,586,546 B2 | 9/2009 | Lee et al. |
| 7,606,613 B2 | 10/2009 | Simon et al. |
| 7,643,862 B2 | 1/2010 | Schoenefeld |
| 7,672,709 B2 | 3/2010 | Lavallee et al. |
| 7,771,436 B2 | 8/2010 | Moctezuma de la Barrera et al. |
| 7,835,784 B2 | 11/2010 | Mire et al. |
| 7,840,254 B2 | 11/2010 | Glossop |
| 7,862,570 B2 | 1/2011 | Russell et al. |
| 7,950,299 B2 | 5/2011 | Burgkart |
| 8,060,184 B2 | 11/2011 | Hastings et al. |
| 8,073,528 B2 | 12/2011 | Zhao et al. |
| 8,109,942 B2 | 2/2012 | Carson |
| 8,114,086 B2 | 2/2012 | Claypool et al. |
| 8,147,503 B2 | 4/2012 | Zhao et al. |
| 8,165,658 B2 | 4/2012 | Waynik et al. |
| 8,167,823 B2 | 5/2012 | Nycz et al. |
| 8,241,296 B2 | 8/2012 | Wasielewski |
| 8,442,621 B2 | 5/2013 | Gorek et al. |
| 8,467,852 B2 | 6/2013 | Csavoy et al. |
| 8,491,579 B2 | 7/2013 | Rossetto |
| 8,516,711 B2 | 8/2013 | Pettersson |
| 8,535,337 B2 | 9/2013 | Chang et al. |
| 8,611,504 B2 | 12/2013 | Kubiak et al. |
| 8,644,909 B2 | 2/2014 | Cooke |
| 8,709,016 B2 | 4/2014 | Park et al. |
| 8,768,437 B2 | 7/2014 | Barrick |
| 8,832,954 B2 | 9/2014 | Atwell et al. |
| 8,961,537 B2 | 2/2015 | Leung et al. |
| 9,119,572 B2 | 9/2015 | Gorek et al. |
| 9,144,470 B2 | 9/2015 | Proulx et al. |
| 9,179,987 B2 | 11/2015 | Goodacre |
| 9,237,885 B2 | 1/2016 | Stein et al. |
| 9,283,047 B2 | 3/2016 | Namiki |
| 9,283,048 B2 | 3/2016 | Kostrzewski et al. |
| 9,341,704 B2 | 5/2016 | Picard et al. |
| 9,452,022 B2 | 9/2016 | McIntosh et al. |
| 9,452,023 B2 | 9/2016 | Boillot et al. |
| 9,510,771 B1 | 12/2016 | Finley |
| 9,532,839 B2 | 1/2017 | Seo |
| 9,554,812 B2 | 1/2017 | Inkpen et al. |
| 9,561,082 B2 | 2/2017 | Yen et al. |
| 9,636,185 B2 | 5/2017 | Quaid et al. |
| 9,639,156 B2 | 5/2017 | Iorgulescu et al. |
| 9,662,179 B2 * | 5/2017 | Nam ................... A61C 1/0023 |
| 9,706,948 B2 | 7/2017 | Bhandari |
| 9,707,043 B2 | 7/2017 | Bozung |
| 9,730,608 B2 | 8/2017 | Lugt et al. |
| 9,750,510 B2 | 9/2017 | Kostrzewski et al. |
| 9,782,229 B2 | 10/2017 | Crawford et al. |
| 9,914,494 B1 | 3/2018 | Meyer |
| 9,925,013 B2 | 3/2018 | Dell et al. |
| 9,964,398 B2 | 5/2018 | Becker et al. |
| 9,974,613 B2 | 5/2018 | Kang et al. |
| 9,986,768 B2 | 6/2018 | Force |
| 10,004,609 B2 | 6/2018 | Palmatier et al. |
| 10,018,706 B2 | 7/2018 | Cisi |
| 10,034,713 B2 | 7/2018 | Yang et al. |
| 10,058,338 B2 | 8/2018 | Shoham |
| 10,080,617 B2 | 9/2018 | Haider et al. |
| 10,105,149 B2 | 10/2018 | Haider et al. |
| 10,136,952 B2 | 11/2018 | Couture et al. |
| 10,176,625 B2 | 1/2019 | Bridges |
| 10,194,990 B2 | 2/2019 | Amanatullah et al. |
| 10,299,874 B2 | 5/2019 | Weitzner et al. |
| 10,350,014 B2 | 7/2019 | Beelen et al. |
| 10,357,184 B2 | 7/2019 | Crawford et al. |
| 10,368,878 B2 | 8/2019 | Lavallee et al. |
| 10,531,926 B2 | 1/2020 | Roessler |
| 2003/0059097 A1 | 3/2003 | Abovitz |
| 2004/0243148 A1 | 12/2004 | Wasielewski |
| 2005/0020909 A1 | 1/2005 | Moctezuma de la Barrera |
| 2006/0142657 A1 | 6/2006 | Quaid |
| 2006/0173291 A1 | 8/2006 | Glossop |
| 2007/0249986 A1 | 10/2007 | Smego |
| 2007/0270686 A1 | 11/2007 | Ritter |
| 2007/0287911 A1 | 12/2007 | Haid et al. |

(56) References Cited

U.S. PATENT DOCUMENTS

| | | | |
|---|---|---|---|
| 2008/0154389 A1* | 6/2008 | Smith | A61B 34/73 901/41 |
| 2009/0076655 A1* | 3/2009 | Blondel | A61B 34/35 700/254 |
| 2009/0177081 A1 | 7/2009 | Joskowicz | |
| 2011/0054293 A1* | 3/2011 | Markowitz | A61B 34/20 600/407 |
| 2011/0275957 A1 | 11/2011 | Bhandari | |
| 2012/0071757 A1 | 3/2012 | Salcudean et al. | |
| 2012/0203092 A1 | 8/2012 | Sweeney et al. | |
| 2012/0319859 A1 | 12/2012 | Taub et al. | |
| 2012/0330367 A1 | 12/2012 | Roche et al. | |
| 2013/0016185 A1 | 1/2013 | Stolka et al. | |
| 2013/0132026 A1 | 5/2013 | Lippuner et al. | |
| 2013/0165947 A1 | 6/2013 | Nguyen et al. | |
| 2013/0169423 A1 | 7/2013 | Iorgulescu et al. | |
| 2013/0172907 A1 | 7/2013 | Harris | |
| 2013/0322726 A1 | 12/2013 | Nathanial et al. | |
| 2014/0107471 A1 | 4/2014 | Haider et al. | |
| 2014/0134586 A1 | 5/2014 | Stein et al. | |
| 2014/0148808 A1 | 5/2014 | Inkpen | |
| 2014/0163557 A1 | 6/2014 | Beyar et al. | |
| 2014/0276871 A1 | 9/2014 | Sherman et al. | |
| 2014/0296860 A1 | 10/2014 | Stein et al. | |
| 2014/0375784 A1 | 12/2014 | Massetti | |
| 2015/0126859 A1 | 5/2015 | Popovic et al. | |
| 2015/0272696 A1 | 10/2015 | Fry et al. | |
| 2015/0302634 A1 | 10/2015 | Florent et al. | |
| 2015/0355310 A1 | 12/2015 | Gong et al. | |
| 2016/0000571 A1 | 1/2016 | Mahfouz | |
| 2016/0022374 A1 | 1/2016 | Haider et al. | |
| 2016/0119529 A1 | 4/2016 | Stoka et al. | |
| 2016/0135816 A1* | 5/2016 | Lavallee | B25J 9/0009 606/88 |
| 2016/0166338 A1 | 6/2016 | Hartmann et al. | |
| 2016/0191887 A1 | 6/2016 | Casas | |
| 2016/0220320 A1 | 8/2016 | Crawford et al. | |
| 2016/0220385 A1 | 8/2016 | Falardeau | |
| 2016/0242934 A1 | 8/2016 | van der Walt | |
| 2016/0338776 A1 | 11/2016 | Jaramaz et al. | |
| 2016/0357260 A1 | 12/2016 | Raynor et al. | |
| 2017/0072557 A1 | 3/2017 | Troy et al. | |
| 2017/0119413 A1 | 5/2017 | Romo | |
| 2017/0245781 A1 | 8/2017 | Kay et al. | |
| 2017/0327371 A1 | 11/2017 | Bai | |
| 2018/0064496 A1 | 3/2018 | Hladio et al. | |
| 2018/0242967 A1 | 8/2018 | Meade | |
| 2020/0197099 A1* | 6/2020 | Xu | A61B 34/20 |
| 2021/0186454 A1* | 6/2021 | Behzadi | A61B 7/023 |
| 2021/0192759 A1* | 6/2021 | Lang | A61B 34/20 |
| 2021/0378627 A1* | 12/2021 | Yarmush | A61B 5/15003 |

FOREIGN PATENT DOCUMENTS

| | | |
|---|---|---|
| CN | 104656095 A | 5/2015 |
| DE | 10333012 B2 | 5/2007 |
| EP | 0730210 B1 | 6/2002 |
| EP | 1570782 A2 | 7/2005 |
| JP | 4265698 B2 | 5/2009 |
| JP | 5763666 B2 | 4/2013 |
| JP | 6370789 B2 | 12/2015 |
| WO | 0180738 A1 | 11/2001 |
| WO | 2009027191 A1 | 3/2009 |
| WO | 2015085011 A9 | 6/2015 |
| WO | 2017059870 A1 | 4/2017 |
| WO | 2020160120 A1 | 8/2020 |
| WO | 2020172397 A1 | 8/2020 |

OTHER PUBLICATIONS

Ajuied et al., "Saw Cut Accuracy in Knee Arthroplasty—An Expiremental Case-Control Study", Journal of Arthritis; pp. 1-5, vol. 4, Issue 1; Published 2015.

Mendes et al., Ethylene oxide sterilization of medical device: A review, Nov. 2007 (Year: 2007).

Andres et al., Laser-guided lumbar medial branch kryorhizotomy, Sep. 2010 (Year: 2010).

* cited by examiner

Drill Handle Base Showing
Internal Electonics Chamber

INSTRUMENT BOURNE OPTICAL TIME OF FLIGHT KINEMATIC POSITION SENSING SYSTEM FOR PRECISION TARGETING AND METHODS OF SURGERY

CROSS-REFERENCE TO RELATED APPLICATIONS

This application is a national stage application, filed under 35 U.S.C. 371, of International Patent Application No. PCT/US2020/019022 filed Feb. 20, 2020, which claims the benefit of U.S. provisional No. 62/808,495 filed Feb. 21, 2019, the entire contents of which are incorporated herein by reference for all purposes.

FIELD OF THE INVENTION

The field of this invention is in the area of medical devices, and more specifically, medical devices used by qualified personnel such as physicians and nurse practitioners, and most notably surgeons of various specialties including orthopedic generalists, orthopedic and podiatric extremity specialists, spinal surgeons, neurosurgeons, oral surgeons, and dentist, during medical or dental procedures, and especially surgical procedures. More specifically, this invention is related to relatively small and cost efficient hand-held surgical devices, such as a drill or wire driver, and tools or apparatus which can be sterilized, or which have a cost structure that would permit single use so that they are "disposable", and to methods of surgery that incorporates such devices. Additionally, this invention permits fine precision control of remotely-controlled robotic manipulators for virtual reality control of instruments and hand tools, such as surgical instruments.

BACKGROUND OF THE INVENTION

While there has been a substantial body of work and commercial products which provide imaging assistance or robotic guidance, (i.e., "surgical navigation") during surgery, the devices have been "large box" devices for example million-dollar devices owned and leased to the practitioner by a hospital or healthcare institution, and that are lodged in dedicated surgical environments. These devices require a very large capital investment, which includes the cost of the surgery room and environmental controls, training for dedicated personal, and an expensive and complex device. Moreover, these devices tend to be large and invasive in the surgery and may even dictate the surgical environment such as the space and temperature requirements around these devices.

Since these "big box" devices include complicated hardware and software and very high development costs, there has been very little development with respect to lower cost hand-held surgical devices with positional feedback, or "targeting systems", for medical use since these devices have limited cost elasticity, and uncertain return on the development and production costs, in addition to cost absorption, payment or reimbursement issues.

Thus, typical "targeting" is presently limited to the hand-eye coordination of the practitioner performing the procedure. As discussed herein "targeting" refers to the guidance in time and through space of the trajectory and depth of an instrument workpiece within a biological environment, which typically involves highly sensitive areas and highly critical positioning and time constraints. Depending on the medical specialty or even the area of the body being treated, the "workpath" may have constraints that include the start point, the end point, and the path between, especially for areas with high concentrations of sensitive and functional or life threatening implications, such as the spine, extremities, the heart or the brain or areas critically close to nerves, arteries or veins. Thus, the invention is intended for use in an area that has a volume ranging broadly from a cubic centimeter to a cubic meter with a radial end point accuracy of less than 3 millimeter, and preferably less than 2 or even 1.5 millimeters.

For procedures in which the precision of the cutting or drilling of a target pathway located within a physical patient body is crucial (i.e., the "workpath"), the skill and hand-eye coordination of the surgeon is of paramount importance. Due to the nature of hand-held tools, and the dynamic and flexible nature of the "work area" within a patient body, errors of the tool tip versus ideal positioning during use can, and will, occur regardless of the skill of the working practitioner. This possibility is increased with user fatigue that can be physical and mental in origin, as well, as issues relating to inexperience, and differing surgical conditions, such as bone or soft tissue quality.

It is the aim of the present invention to reduce these errors by providing the surgeon with a real-time indication of the "workpath" of the tool relative to the anatomical site. In certain types of surgery, real-time radiography using x-rays provides the surgeon with the knowledge of positional information that would otherwise by invisible due to the opaqueness of the site. However, this is not always possible, and certainly, it is not desirable to use radiography in real-time as the exposure to x-rays can be considerable for both the patient and the surgeon. Thus, it is desired that the position of the tool tip relative to a desired "workpath" be provided by a means that minimizes any health risk as a result of the surgery to the patient or surgeon.

SUMMARY OF THE INVENTION

The present invention addresses the need for a device which is distinguished from the prior art high capital "big box" systems costing hundreds of thousands of dollars and up. This invention further relates to a method for the accurate real-time positional determination in three dimensions of a surgical instrument workpiece relative to the end point or pathway within the patient body (i.e., the "optimal course" or "workpath" of the instrument workpiece) in the operating room, for procedures including, among other things, drilling, cutting, boring, planning, sculpting, milling, debridement, where the accurate positioning of the tool workpiece during use minimizes errors by providing real-time positional feedback information during surgery and, in particular, to the surgeon performing the procedure, including in an embodiment in line of sight, or in ways that are ergonomically, advantageous to the practitioner performing the procedure.

In a narrow recitation of the invention, it relates to a guidance aid for use by orthopedic surgeons and neurosurgeons that is attached to a standard bone drill or driver and operates so as to provide visual displayed feedback to the surgeon about how close the invasive pathway is during the drilling operation to an intended orientation and trajectory. Thus, the invention permits the surgeon to use the visual feedback to make course corrections to stay on track, and as necessary to correct the trajectory of a workpiece. In the past, surgeons would use a mechanical "jig" to help guide the position of the intended starting point, and the end point of a drill pathway (i.e., the drill hole), but the present invention uses electronic, and preferably optical time-of-flight (OTOF) sensors in collaboration with inertial measurement units (IMUs) and a digitally encoded extendable link or cable, the so-called "Draw-Wire" sensors, that are borne by a hand-held instrument with a visual display and feed-back system to inform the surgeon as to how to create a drill pathway through a subject patient body part which is contained within a three dimensional reference frame. By "hand-held", it is meant an instrument that weighs under five pounds and has a configuration that allows it to be manipulated in the hand of a user. Reference points are obtained such as through digital images, for example, captured using fluoroscopy.

The system of the invention establishes a frame of reference for the anatomical subject area to allow a user to mark reference points through the placement of markers (e.g., pseudorandomized cloud point fiducials) to define a calibration of the absolute position of the hand-held sensor relative to the physical. The reference system that also includes the patient and a side plane, and an independent imaging system is used to visualize the anatomical site, while the system includes means to determine, and mark starting and end points relative to the anatomical subject area and input them into the reference system. The guidance system works within the marked reference area to determine the location of sensors, preferably OTOF, and kinematic IMU, and Draw-Wire sensors, carried on the hand-held instrument which is linked by a flexible and extendible rod or cable to a base tied to the surgical site at a known relationship.

Thus, the invention relates to a surgical targeting system guided by OTOF and kinematic sensors that are strategically mounted on the hand-held (or potentially robotic) drill. The sender receiver pairs are in proximity to x-ray opaque fiducials which are positioned relative to the subject surgical area (i.e., the anatomy of the patient which is located within a defined three-dimensional reference frame) and which determine the proximity in space of the associated OTOF and kinematic sensors as they change course over time. The markers and the drill entry and end points are selected by the user (surgeon) and entered into a computer program residing on a CPU member that accesses software to display or represent the drill pathway of the surgical workpiece in the subject surgical area on a GUI ("graphical user interface") as determined by the relationship between the OTOF transceiver with the reference frame of the system. Thus, the system allows the display to inform the user as to the trajectory of the instrument and the depth of penetration into the anatomical site which can be displayed in a number of ways, including reticles or cross-hairs, circle in circle, numbers, colored lines showing the desired and actual course or vector, or other alignment methods including in separate visuals or combined.

In accordance with the present invention a plurality of OTOF (Optical Time of Flight) sensors acting as light pulse transceivers are mounted to the tool handle and relative to a reference frame that is represented by a base plate which is positionally fixed relative to the surgical site (i.e., the physical environment within or about the patient's body). In this case, the surgical site may also need to be positionally fixed or restrained within the reference frame. An electronic microprocessor system synthesizes the light pulses which are generated by the OTOF transceiver sensors, along with kinematic position and digitizes the measured received light pulses and performs the necessary algorithms such as FFTs (Fast Fourier Transform), correlation functions, and other digital signal processing (DSP) based algorithms performed in hardware/software, thus provides the real-time positional information for the surgeon for example, via an electronic screen such as in "line of sight" on the tool handle itself or on a separate monitor, including a display that could be linked to the system, such as on a head's up display screen worn by the surgeon or a dedicated display that is located at a position that is ergonomically advantageous for the user. The tool can be any tool used by a medical practitioner, including for example, a scalpel, saw, wire driver, drill, laser, arthroscope, among others.

In the simplest embodiment of this invention, the tool handle will support and/or house a plurality of the OTOF transceivers mounted in an orthogonal fashion along with an IMU and draw-wire sensor system such that 5 degree of freedom (DOF) information regarding the linear (x, y, z) position, and the angular (yaw, pitch) can be obtained from the knowledge of the vector positions. At a minimum there is 1 OTOF transceiver, an IMU, and a draw-wire sensor, but preferably 3 OTOF transceivers to provide redundancy.

By means of the targeting assistance provided by the present invention, it is further desired that 5 degrees of freedom (DOF) positional information be provided in real-time at rates of up to 3, preferably 2 and most preferably 1 per second, with a positional accuracy of +/−3 mm, preferably 2 mm, and most preferably 1 mm, in 2 or 3 linear dimensions, and angular accuracy of +/−3° and preferably 2° in 2 angular dimensions of pitch and yaw, and that this positional information be obtainable in a 0.75 m×0.75 m×0.75 m, and preferably 0.5 m×0.5 m×0.5 m cubic working volume.

In the present invention, a plurality of OTOF transceivers (i.e., at least 3 and more precisely from 3 to 15, or 3 to 10 where the excess from a three-dimensional matrix are used for an array) are used to provide the positional information of a tool relative to a mechanical reference plane supported or mounted relative to or on the tool. The distances from the transmitters to the transceivers are calculated either by a time-of-flight (TOF) propagation of the transmitted sound pulse, or based on the phase information from the Fast Fourier transform (FFT) of the light waves emitted from the transmitter(s) onto the receiver(s) on the OTOF sensor. This phase information is proportional to the time delay of the transmitted pulse to the received sound pulse. With the use of the speed of light, a distance from the OTOF transceiver can be calculated. Internally, to the OTOF sensor, the use of phase extraction from optical heterodyne techniques provides some immunity to amplitude noise as the carrier frequency is in the MHz range and well above the usual 1/f noise sources. The use of certain coding schemes superimposed upon the carrier frequency permits the increase in signal to noise ratio (SNR) for increased immunity to ambient noise sources. Other means of extracting distance or positional information from ultrasonic transducers for robotic navigation have been described by Medina et al. [2013], where they teach that via use of a wireless radio frequency (RF), coupled with ultrasonic time-of-flight transducers, positional information with up to 2 mm accuracy can be obtained in a space as large as 6 m for tracking elder movement. Segers et al. [2014, 2015] has shown that ultrasonic pulses can be encoded with frequency hopping spread spectrum (FHSS), direct sequence spread spectrum, or frequency shift keying (FSK) to affect the determination of positions with accuracies of several centimeters within a 10 m space. More recently, Khyam et al. [2017] has shown that orthogonal chirp-based modulation of ultrasonic pulses can provide up to 5 mm accuracy in a 1 m space. Liao et al. [2010] showed that image guided surgery (IGS) could provide accuracies up to 2.5 mm. A more recent review of various IGS techniques shows a survey of prior-art techniques that combine image processing and radiography to enhance surgery outcomes via an improvement of the instrument placement accuracy. However, none of these previous studies have been able to provide a 2 or 1 mm accuracy for a system that fits within an operational size space that is the size of the intimate volume directed affected by most medical procedures (i.e., about 1 cubic meter or less), which is the goal of the present invention.

In a more advanced embodiment, the tool and the base for the workpiece can also contain visual fiducial markers that will assist a double set of video cameras mounted orthogonally as to produce a top view and a side view so that the fiducial markers can be used with video image processing to deduce spatial information that can be used in conjunction with the OTOF sensors for positional information.

And in yet a further advanced embodiment, the digital signal processing (DSP) and sensor fusion of the various data streams from the OTOF, IMU, and draw-wire sensors will provide a precision virtual reality high-dexterity effector to allow precision remote-controlled operations requiring great dexterity and control of a tool or instrument such as: surgery, bomb-defusing, spacecraft repair, etc.

In a third embodiment, the OTOF and kinematic sensor system above is used in conjunction with a fluoroscopic radiography system to provide both contextual imaging, coupled with quantitative positional information for the most critical types of surgery (which can include spinal surgery, invasive and non-invasive neuro surgery or cardiac surgery, for example). Thus, the invention also relates to methods of performing medical procedures including surgery and dentistry that establishes and frame of reference for the anatomical site, and wherein a medical tool supports sensors to locate and guide a medical procedure on the anatomical site within the frame of reference. As an example, the present invention relates to a procedure involving a guided procedure to percutaneously implant guide wires in a femoral neck for a non-invasive cannulated screw fixation of a hip fracture.

All of the above embodiments allow for the real-time display of the absolute positional information of the tool workpiece and preferably the tool tip, relative to the body part, intended target position, and the desired "workpath". The display could show a delta distance reading relative to the intended target position so that the surgeon is simply looking to minimize the displayed delta numbers or a graphical or other visual representation thereof (e.g., circle in circle). The display will show the x, y, z positions to the nearest millimeter or partial millimeter and also the yaw and pitch to the nearest degree or partial degree, including the incremental changes of these values. The angle of approach is often an important parameter for certain procedures such as a wire drill and especially where the start point may be known, and the end point maybe marginally understood, but the path between may only have certain criteria.

It is also the aim of this invention to provide this positional information in a lightweight tool handle that is unobtrusive and easy to use, and as similar to the existing instrument as possible, such that the transition to use of the system of the invention is user friendly and seamless to the practitioner. It is a further goal of this invention to have a tool handle and base plate with transmitters that are easy to sterilize, including by autoclave, or which are cost-effective enough for manufacture in whole or in part, as a disposable one-time use system.

It is one advantage of the present invention that it can be very compact and unobtrusive by nature of the form factor, and the possibility of being wireless, and the positional sensing is effected by light and a single absolute distance kinematic sensor compared to mechanical position sensors such as articulated multi-joint angular-feedback linkages, and further that the invention can be safely used in a healthcare facility without hindrance by external noise or without contaminating other wave uses in the facility.

Another advantage of the present invention it permits the surgeon to manually hold the tool in a natural manner that does not have any mechanical resistance, such as that might be encountered with as articulated multi-joint angular-feedback linkages, and with a footprint and size that can be easily manipulated and which is similar so much as possible to the tools that they are already comfortable using.

It is another advantage of the present invention that it can provide both position and angular information simultaneously, and advantageously, sufficiently in 'real-time" to enable the use during surgery.

It is another advantage of the present invention that it has immunity over typical ambient background noise sources since it works in the near infrared wavelength band, and the data processing occurs via FFT in the frequency domain where typical mechanical and ambient noise source amplitudes are minimized through the 1/f principle where noise amplitude is inversely proportional to the noise frequency.

It is another advantage of the present invention that it can be used to augment radiography techniques such as fluoroscopy or x-rays to provide an additional level of information that is quantitative and can be used for the "last inch" deployment of a surgical tool for critical procedures where accuracy is of paramount importance.

It is another advantage of the present invention that it provides the surgeon with positional sensing system that is absolute relative to the working base reference system and is free from dead-reckoning (propagation-based) errors that are inherent in some other types of (non-absolute) positional sensing.

It is an additional advantage of the system that it serves as a three dimensional aiming system that a single use or low cost hand-held instrument includes a system that helps the user (a surgeon or robot) determine the work angle for a workpiece integral to the instrument from an identified point of entry in an anatomical work area to a desired end and provides haptic feedback by display or tactile means to correct the alignment of the workpiece to achieve and/or maintain the desired alignment. The system can be used in surgery, or for training purposes, with an instrument, such as a drill or wire driver or for the implantation of implants including pegs, nails and screws. Examples of suitable surgical method using the present invention include hip fracture fixation where a screw of nail is inserted into the greater trochanter using the present targeting, aiming or guidance system or instrument, or for use in hammer toe fixation which can include phalangeal intermedullary implants.

DETAILED DESCRIPTION OF THE INVENTION

Figure 1:
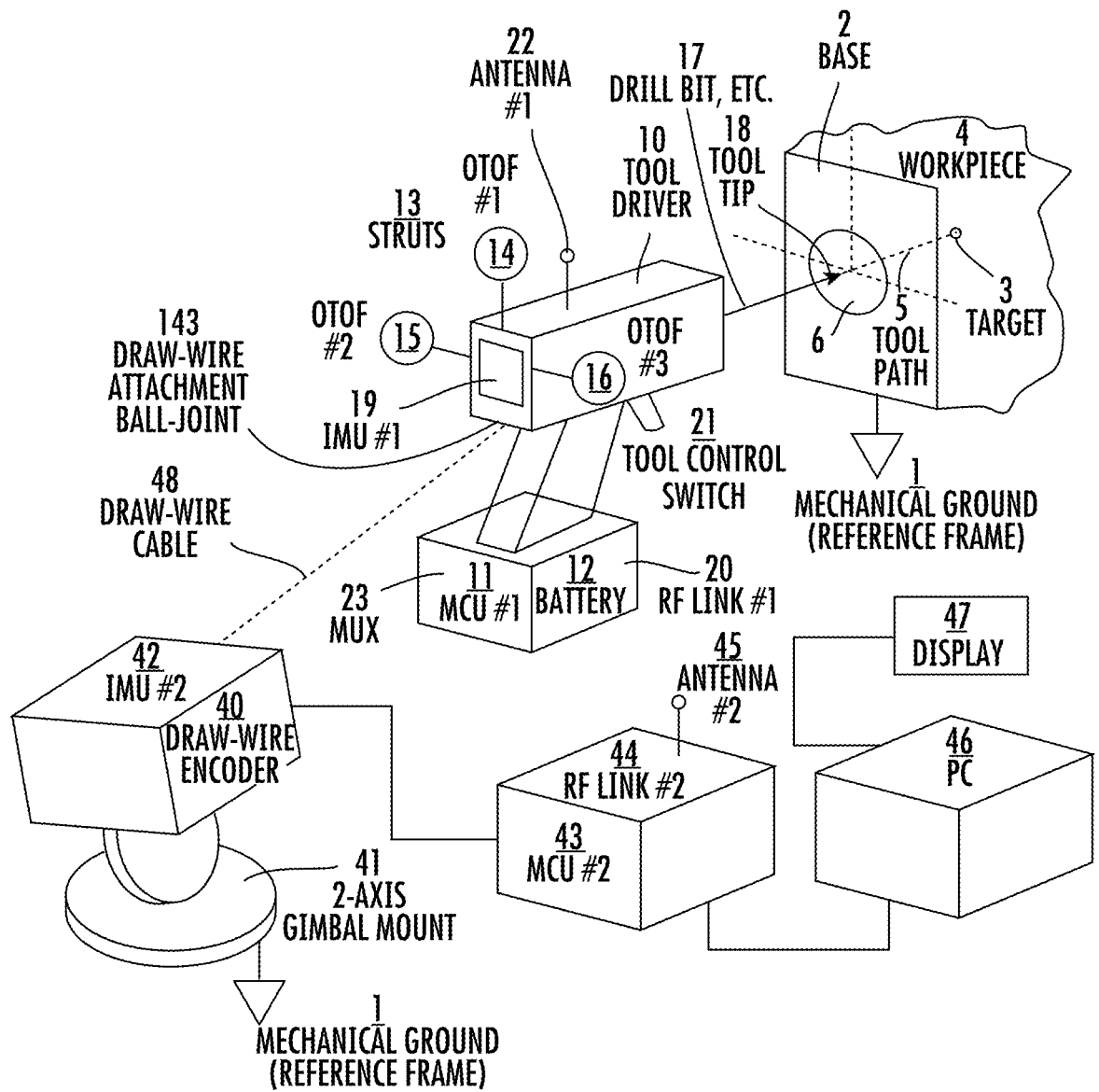
FIG. 1 shows a schematic diagram of the preferred embodiment of the present invention.

In the preferred embodiment of the present invention as shown by the schematic diagram in FIG. 1, a tool driver 10, fitted with struts (supporting rods) 13 that serve to hold at least three OTOF transceiver at the top 14, left 15, and right 16 positions. The tool driver 10 has a tool control switch 21 and a tool bit (k wire, drill, scalpel, etc.) 17, which has a distal tip 18 which corresponds to the spatial positional information shown in the display 47. The transceivers 14, 15, 16 (e.g., Sparkfun VL53LOX) are in optical communication with an optically reflecting flat base 2. These optical transceivers are optically linked to a rigid base plate 2 that serves to locate the transmitters with respect to the workpath in the surgical environment in the patient's body part 4 subject to the procedure, to guide the tool tip 18 through an aperture 6 in the base 2, along the workpath 5, towards the target 3. The OTOF transceivers, IMU 19, are in direct or indirect electrical communication with an electronic microller unit #1 (MCU #1) 11 to a controller PC (or "CPU", i.e., a computer processing unit), 46 via physical wiring cable or by radio frequency electronic transmission, such as Xbee or Bluetooth via RF transceivers 20 and 44 via antennas 22 and 45 and MCU #2 43. A draw-wire encoder 40 mounted on a rotating 2-axis gimbal mount 41 and physically linked through a flexible and extensible link, such as a mechanical tape, wire, rod, or most preferably cable 48 between the draw-wire encoder 40 and the tool handle 10, provides the absolute mechanical distance from a fixed reference mechanical ground point 1 to the target 3. The draw-wire encoder 40 also is fitted with an NU #2 42 to provide the azimuth and elevation angles that are transmitted to the MCU #2 43 via wires and then to a PC controller 46 which performs calculations in software to fuse the data generated by the OTOF sensors, the two IMUs, and the draw-wire sensor into a real-time display of the positional information for the surgeon to use as feedback of the tool tip 18 position. Together, these components shown in FIG. 1 form the basis of the present invention's preferred embodiment that utilizes the measurement of the TOF ("Time of Flight") of a light pulse from the transceivers 14, 15, and 16. By use of geometrical relationships, the fixed distances between the individual receivers and transmitters, and the speed of light, the angles of the OTOF relative to the draw-wire axis 42, the precise distances between the spatially separated transmitters and receivers can be determined with a closed form equation calculated either in the MCU #1 11, the computer 46, or even through use of a microcontroller MCU #1 11 in the tool driver 10 itself and then displayed on the screen 47. In this sense, the system can be predictive of the continued course of the tool-tip along the workpath, although, it should be understood that the system tracks the position and displays it in near-real time during use.

Figure 2:
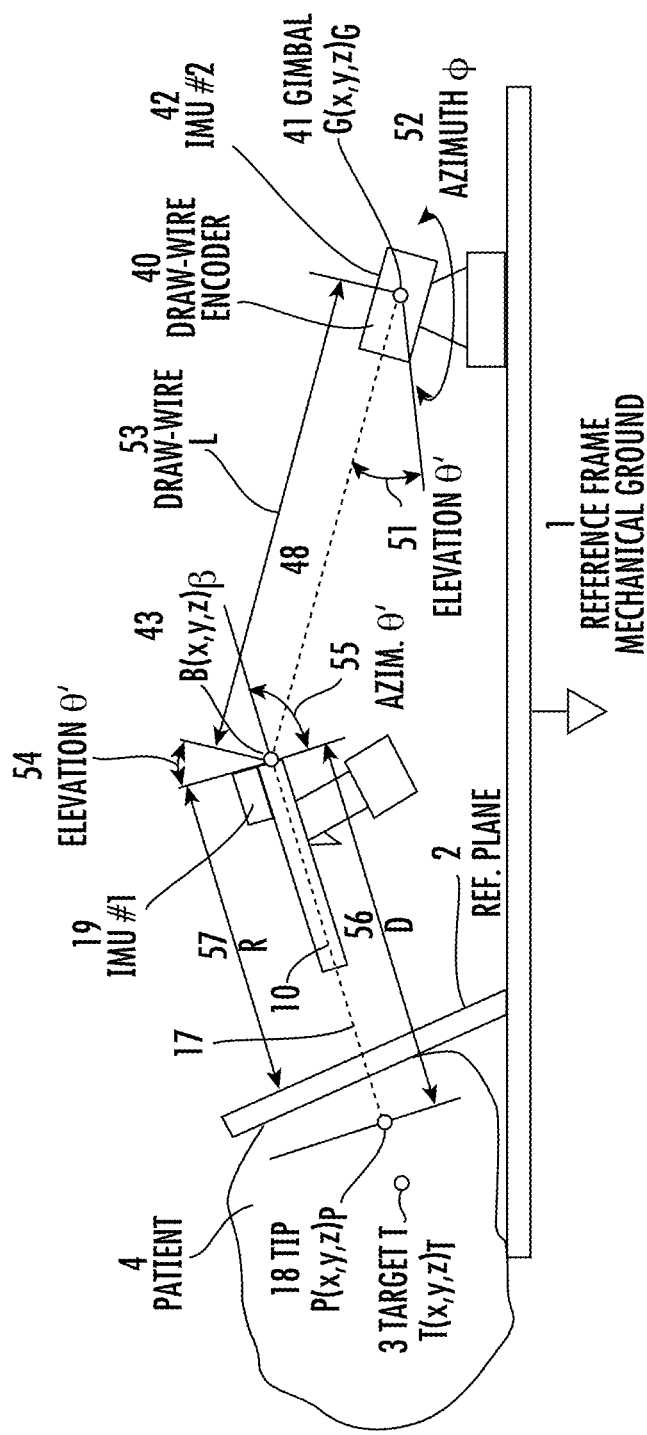
FIG. 2 shows a schematic diagram of the principle of operation.

FIG. 2 schematically illustrates the principle of operation of the present invention. Here, the drill handle 10 along with drill shaft 17, draw-wire sensor 40, IMU #1 19 and IMU #2 42 form a completely deterministic 2-link mechanical linkage system described by the so-called forward kinematic equations that are used for traditional serial link robotic arm analysis. Here, in FIG. 2, the arms have rotating joints located at 143 and 41 are free to move in elevation θ 51 and azimuth φ 52 at the gimbal joint 41 and in elevation θ' 54 and azimuth φ' 55 at the ball-joint attachment point 143. The elevation and azimuthal angles are provided by the IMU's 19 and 42 which are fitted with micro-electro-mechanical systems (MEMS) gyroscopes, accelerometers and magnetometers to effect angular measurements with 0.02 deg accuracy and essentially zero angular drift. In FIG. 2, the knowledge of the variable length L of the draw-wire 53, plus the distance from the drill tip 18, to the ball joint 143, plus the elevation and azimuthal angles at each joint as described above, completely describes the position of the tip 18, relative to the target T point 3 at $(x, y, z)_T$, and its trajectory as described by a vector transecting the points B at $(x, y, z)_B$ and T at $(x, y, z)_T$. The position of any point in a serial chain of links can be described a transformation matrix as described by the so-called Denavit-Hartenberg parameters described elsewhere by Hartenberg and Denavit (1964). The OTOF distance sensors mounted on the drill handle are located at a distance R 57 from a reference plane 2 that is mechanically fixed to the patient 4 with target T 3, with both the patient 4, the reference plane 2, the gimbal 41 are all mechanically grounded to the reference frame 1. In this way, the relative position of the drill tip P 18 located at $(x, y, z)_P$ and the target T 3 located at $(x, y, z)_T$ relative to the gimbal origin point G 41 located at $(x, y, z)_G$ are always known via the forward kinematic equations plus the absolute distance from the point B $(x, y, z)_B$ to the reference plane 2 (as well as the distance D 56 from the point B $(x, y, z)_B$ to the target T at $(x, y, z)_T$) are also know to permit a redundant measurement of distance for error checking. Note that through the use of three OTOF sensors, the angle of the drill vector 17 relative to the reference plane 2 is also known and this provides a redundant measurement of the angle of approach as measured from the NU sensors.

Figure 3:
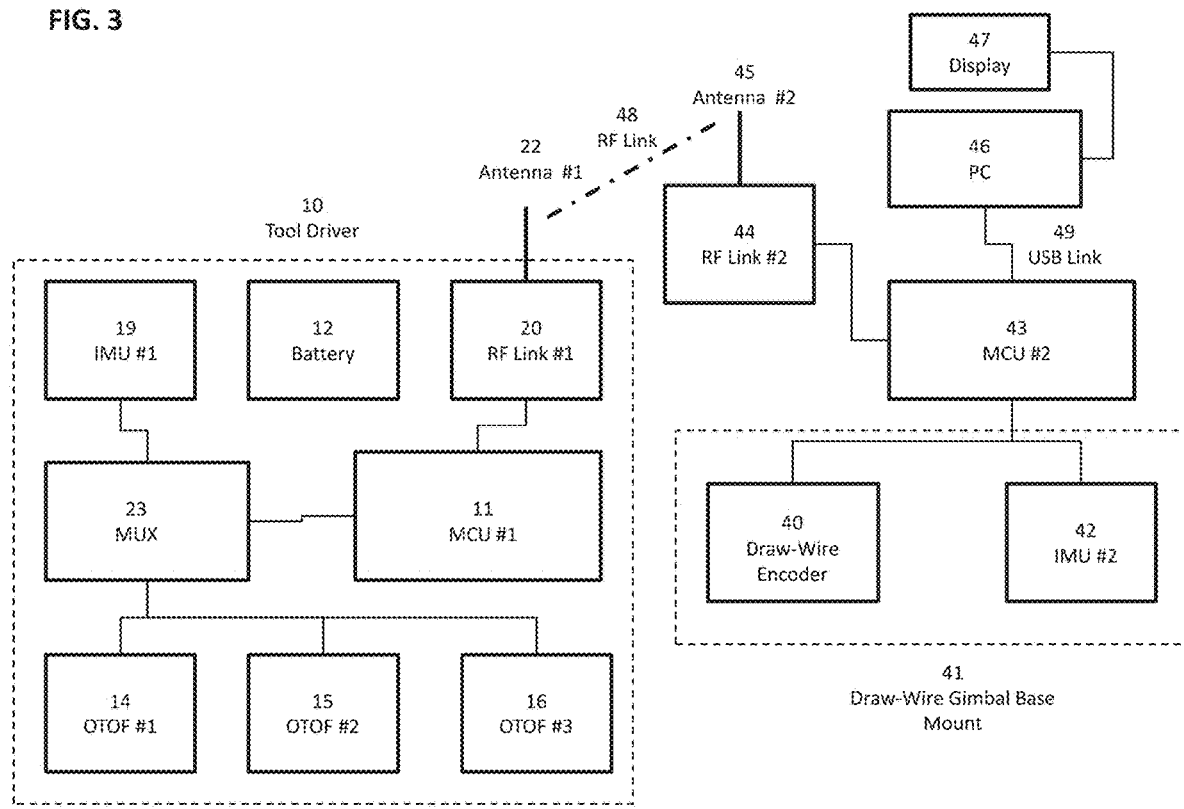
FIG. 3 shows a block diagram of the electronic system.

FIG. 3 shows a schematic block diagram of the electronics and their interconnections for the present invention. The tool driver 10 shown by the dashed box contains the following electronic components which when connected, provide a measurement of the distances from the OTOF sensors 14, 15, 16 which are multiplexed through a MUX 23, and the angular orientation data provided by the IMU #1 19 which are all fed to a MCU #1 11 connected to a wireless RF transceiver link #1 20 fitted with an antenna #1 22. All components in the tool driver 10 are powered by a battery 12.

The battery can be rechargeable or of the primary type. The antenna 22 transmits the data in the drill handle 10 via an RF link 48, to a second RF link #2 44 also fitted with an antenna #2 45. The RF link #2 45 then sends the wireless data from the tool driver 10 to a second MCU #2 43 which also collects data from draw-wire base 41 which contains the draw-wire encoder 40, and the IMU #2 42, and all these data are then processed and fused together via a software program (such as MATLAB or Python) in a PC computer 45 via a USB link 49. It is also possible to replace MCU #2 43 with a more powerful MCU or a single board computer (SBC) to affect the calculations performed in the PC 46. The final positional information and angular data are then presented to the operator via display screen 47.

Figure 4:
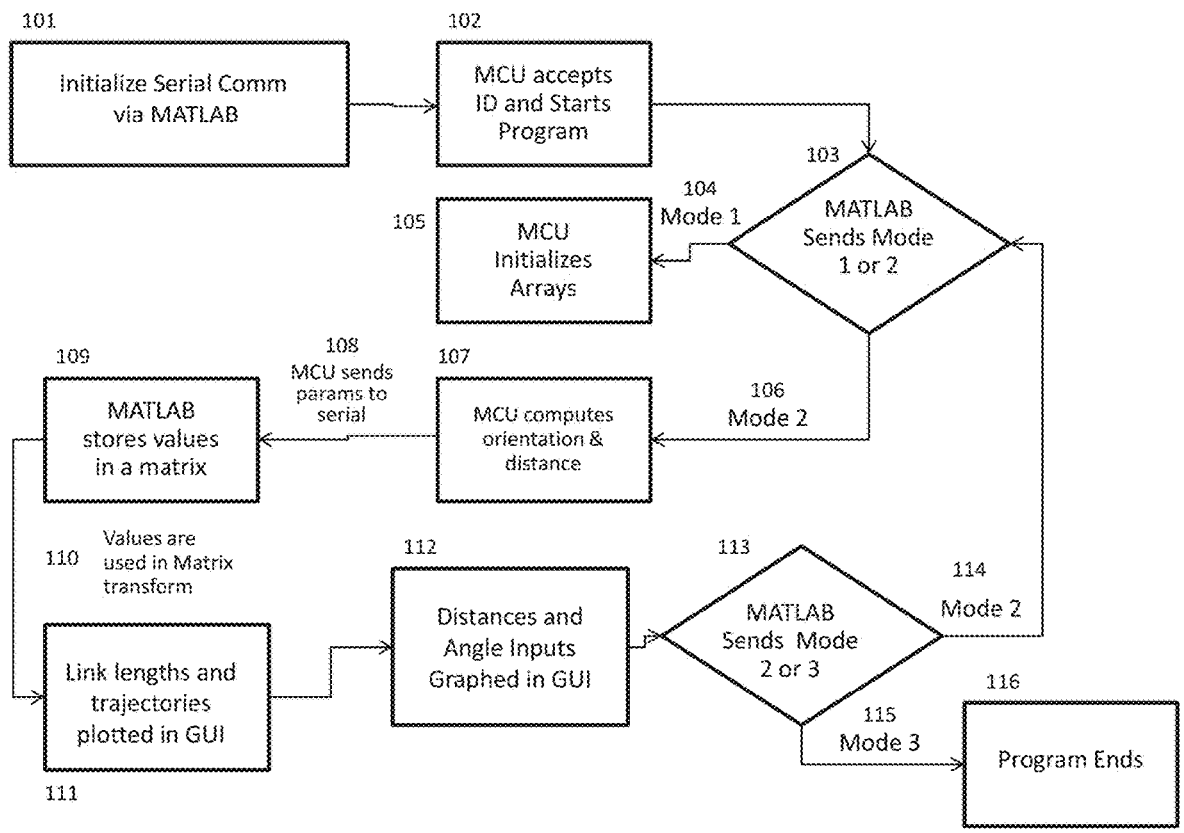
FIG. 4 shows a block diagram of the steps and sequence used to acquire and derive the distances and angles from the sensor data that are generated and collected.

FIG. 4 shows a block diagram of the top level software steps used to calculate and derive the spatial measurement using the system depicted in FIG. 1. In the first Step 101, the MATLAB program initializes the serial communications interfaces between all of the interconnected devices, and in Step 102, the MCU's accepts an identification number and starts the program. In Step 103, the MATLAB program sends a Mode 1 104 or Mode 2 depending on whether or not the program is starting and being initialized. In the case of a start of initialization, Mode 1 is selected which then initialized all of the arrays in the MCU's in Step 105. Once that is done, Mode 2 is selected by the MATLAB program in Step 106 and the MCU's record in Step 107 the orientation and raw distance data from the sensors, whereupon the MCU sends the parameters to the MATLAB program via a serial link in Step 108. In Step 109, the MATLAB program stores the values in a matrix, and these are used in the matrix transformation in Step 110 as described by the so-called forward kinematic equations. The MATLAB program then plots the link lengths and trajectories in a graphical user interface (GUI) in Step 111, whereupon the distances and angle inputs are then graphed on the GUI in Step 112. Depending on whether more data is needed or the sensors need to be stopped in Step 113, the MATLAB program sends a Mode 2 Step 114 to continue the measurement cycle or a Mode 3 in Step 115 to shutdown and stop the program execution in Step 116.

Figure 5:
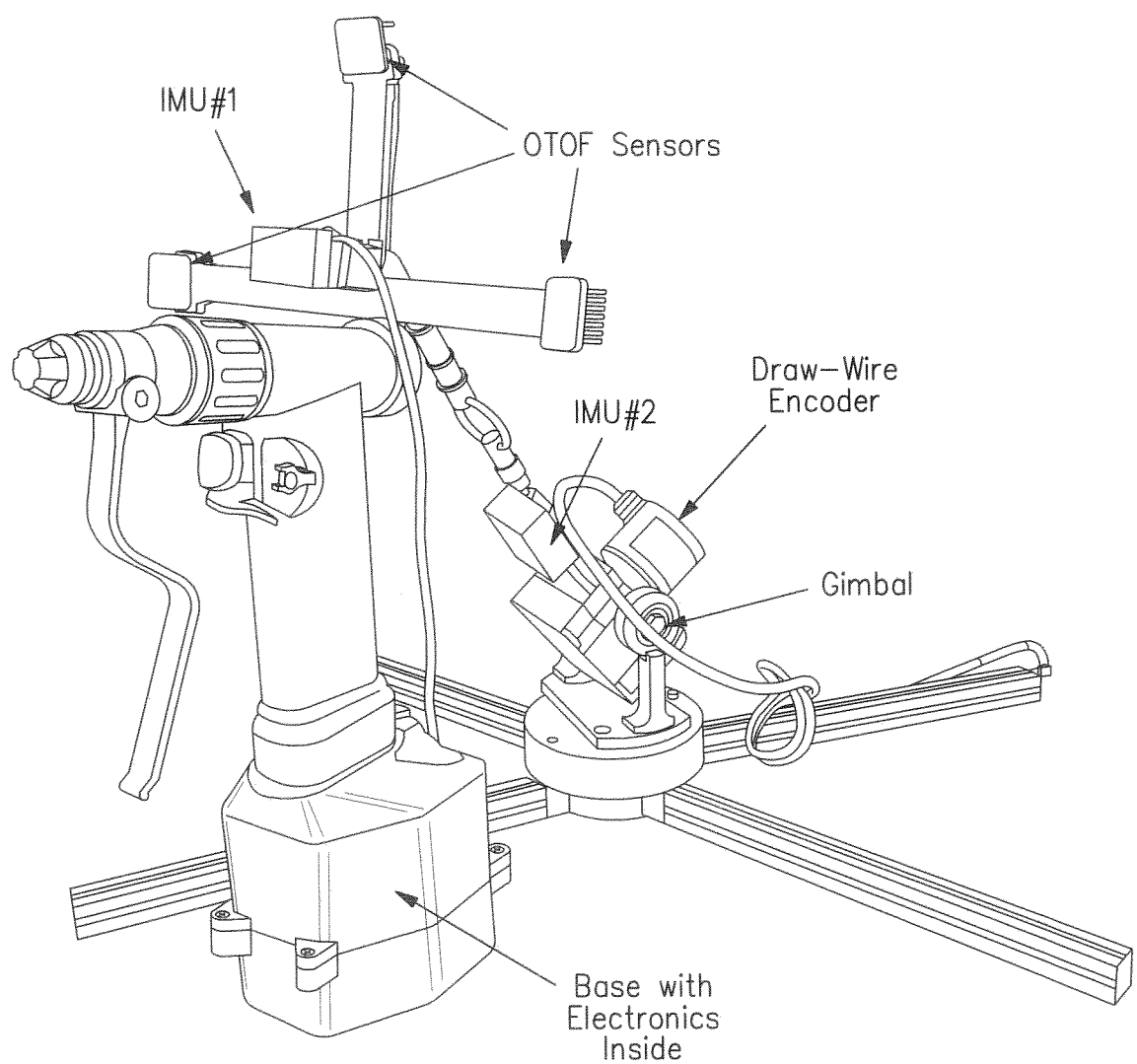
FIG. 5 shows a photograph of a prototype of one embodiment of the present invention reduced to practice.

FIG. 5 shows a photograph of the prototype of the present invention as reduced to practice. In FIG. 5, there are notations showing the locations of the OTOF sensors, the IMU #1, IMU #2, the draw-wire encoder, the gimbal base, and the drill handle base with electronics mounted inside.

Figure 6:
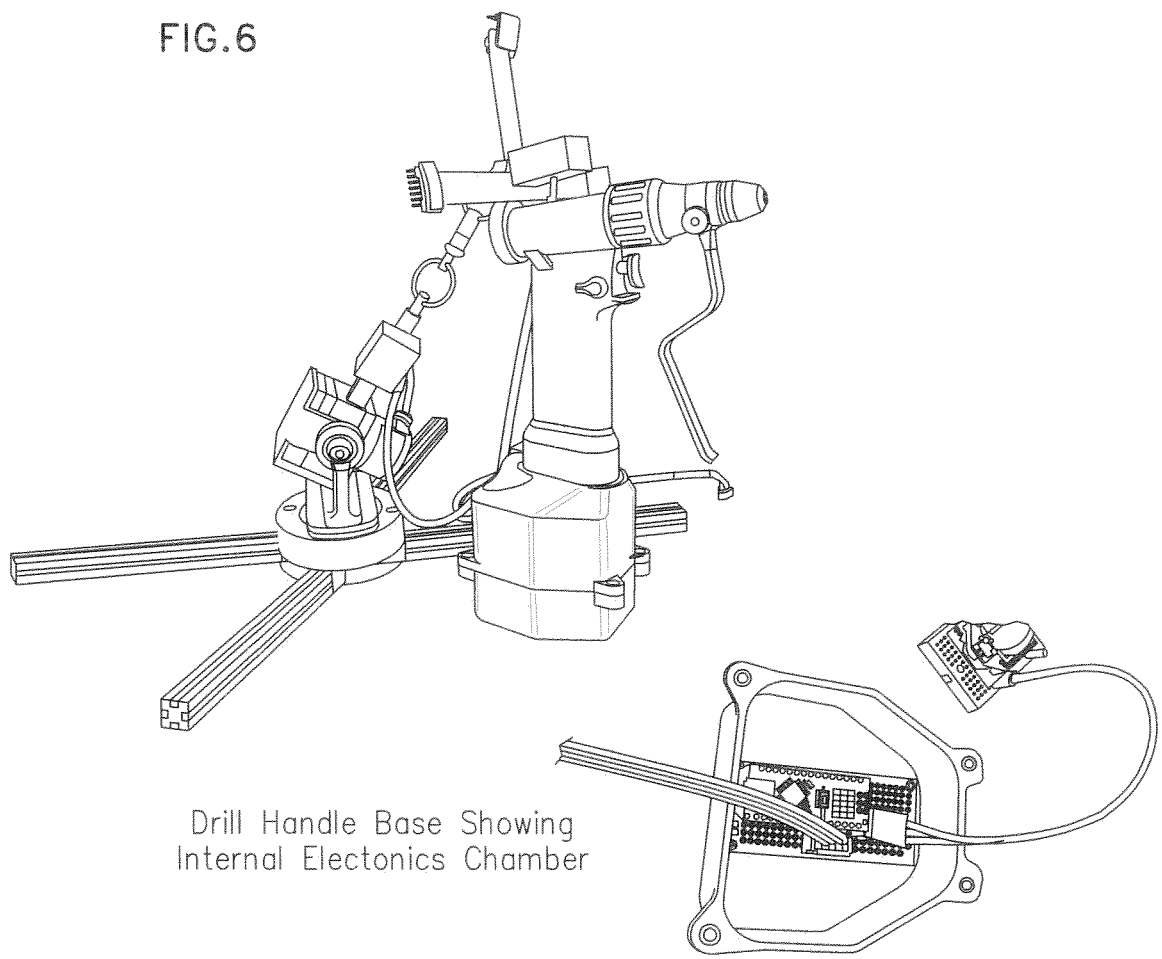
FIG. 6 shows a photograph of the prototype of the present invention reduced to practice with a detail showing the internal electronics in the base of the tool handle.

FIG. 6 shows another photograph of the present invention as reduced to practice but shown from a different perspective for better clarity. Of note is a detail of the drill handle base with the cover removed to show the MCU #1 inside.

Figure 7:
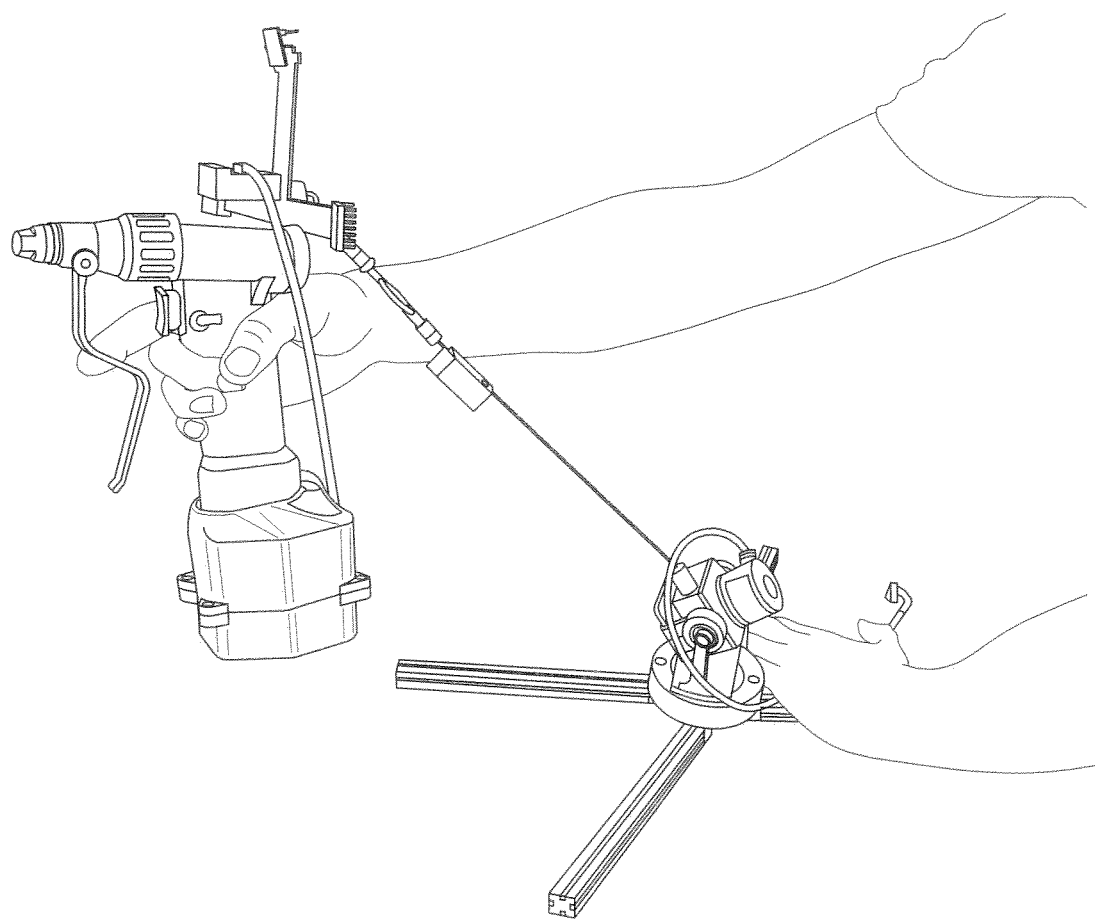
FIG. 7 shows a photograph of the invention reduced to practice and held in a hand to demonstrate the ergonomic aspects.

FIG. 7 shows another photograph of the present invention as reduced to practice but being hand-held to show the relative positioning of an example of where the draw-wire encoder is located and how the gimbal mount allows the draw-wire orientation to be determined with an IMU #2 mounted in the gimbal head.

Analysis of the theoretical best accuracy of the positional determination using a first order angular resolution and moment-arm approach with the measured standard deviations from the IMU angular sensors (+/−0.02 deg) and variable length link arm from the draw-wire sensor (+/−0.5 mm), yields an approximate overall positional uncertainty in radial distances (x,y) of the drill tip to be +/−0.33 mm and axial distance (z) of the drill tip to be +/−0.71 mm. The present prototype embodiment is illustrated having relatively low-tolerance, non-rigid 3d printed plastic mounts used for the mechanical linkages, however, these will be replaced with precision low-backlash machined metal joints, to improve accuracy and to tend towards the theoretical limits shown above.

Analysis of the angular uncertainties of the IMU sensors yields and approximate angular uncertainty of +/−0.03 degrees in elevation (pitch) and azimuth (yaw).

Figure 8:
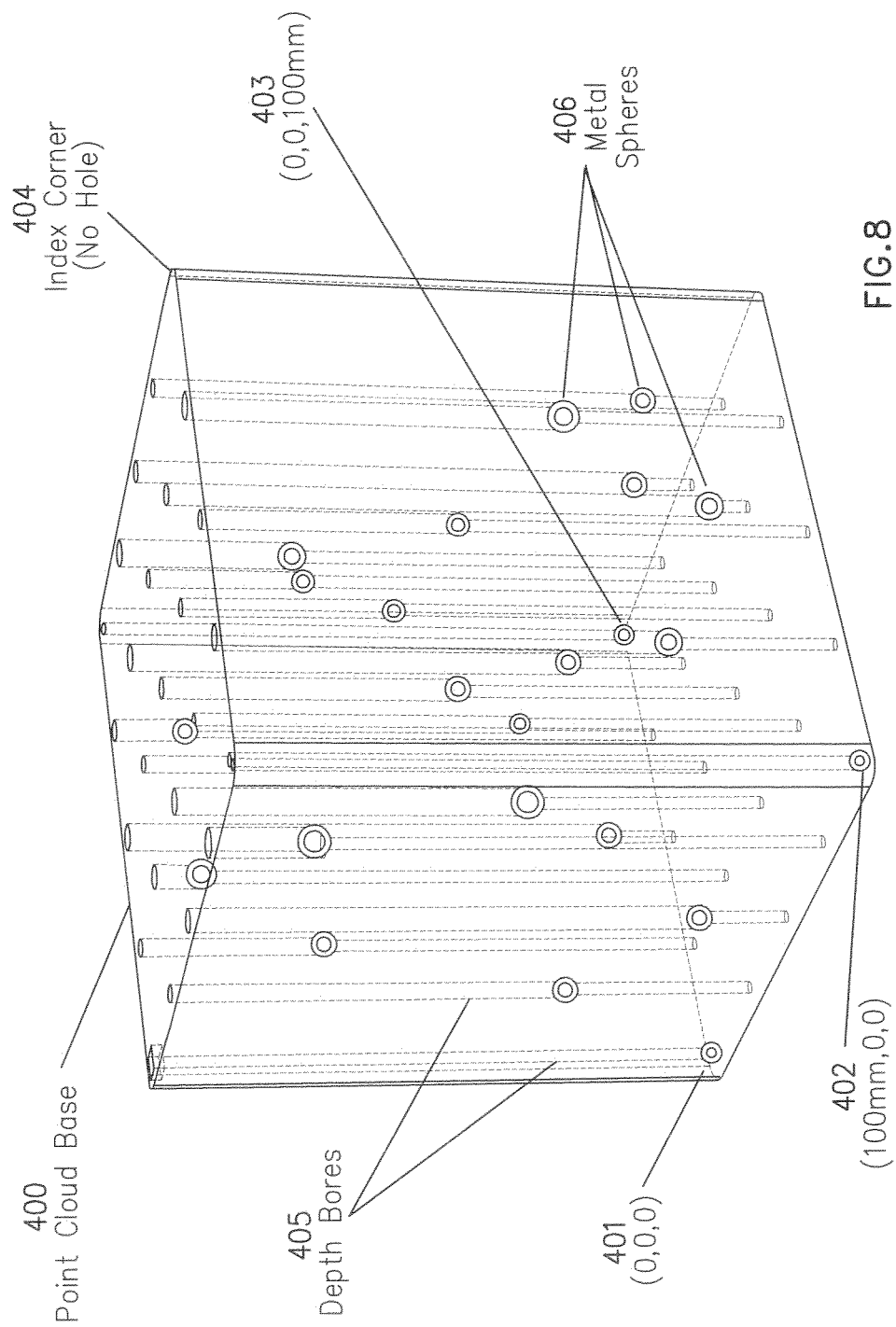
FIG. 8 shows a 3-dimensional point-cloud fiducial reference system for registering the present invention's coordinate axis system with the global coordinate axis system.

FIG. 8 shows a 3-dimensional point-cloud fiducial base 400 that can have, for example, the shape of a cube with precision-depth bored holes 405 which support a plurality of metal spheres 406 of various diameters. At minimum, 3 spheres are required, with typically 8 to 12 spheres being desirable for the accurate calculation of the coordinate system position and orientation via a plurality of orthogonal X-ray images. The sphere positions are strategically chosen as pseudo-random (x, y, z) coordinates in such a way that their X-ray projections at two orthogonal axis do not occlude each other. Three of the spheres 401, 402, 403, preferably of the smallest diameter circa 2 mm are located on the bottom face of the fiducial cube at the (0, 0, 0), (100 mm, 0, 0) and (0, 0, 100 mm) positions to establish a reference frame with which to register against a flat reference surface representing the global coordinate system frame. A global coordinate system or frame of reference is defined as the frame of reference of the operating room as connected to the earth's surface. The local coordinate system or frame of reference is defined as the coordinate system associated with just the mechanical base 1 of the present invention. The metal spheres 406 have various diameters (e.g., 2 mm, 3 mm, 4 mm, 5 mm) to aid in the identification of the orientation relative to a known arrangement within the cube. The cube should have a visual indicator 404, such as one corner that is not bored as a visual index for the user to place with a known orientation. Each sphere inside the fiducial base is at a precisely known position and these position coordinates can be used with fluoroscopy using a C-Arm apparatus as shown in FIG. 9.

Figure 9:
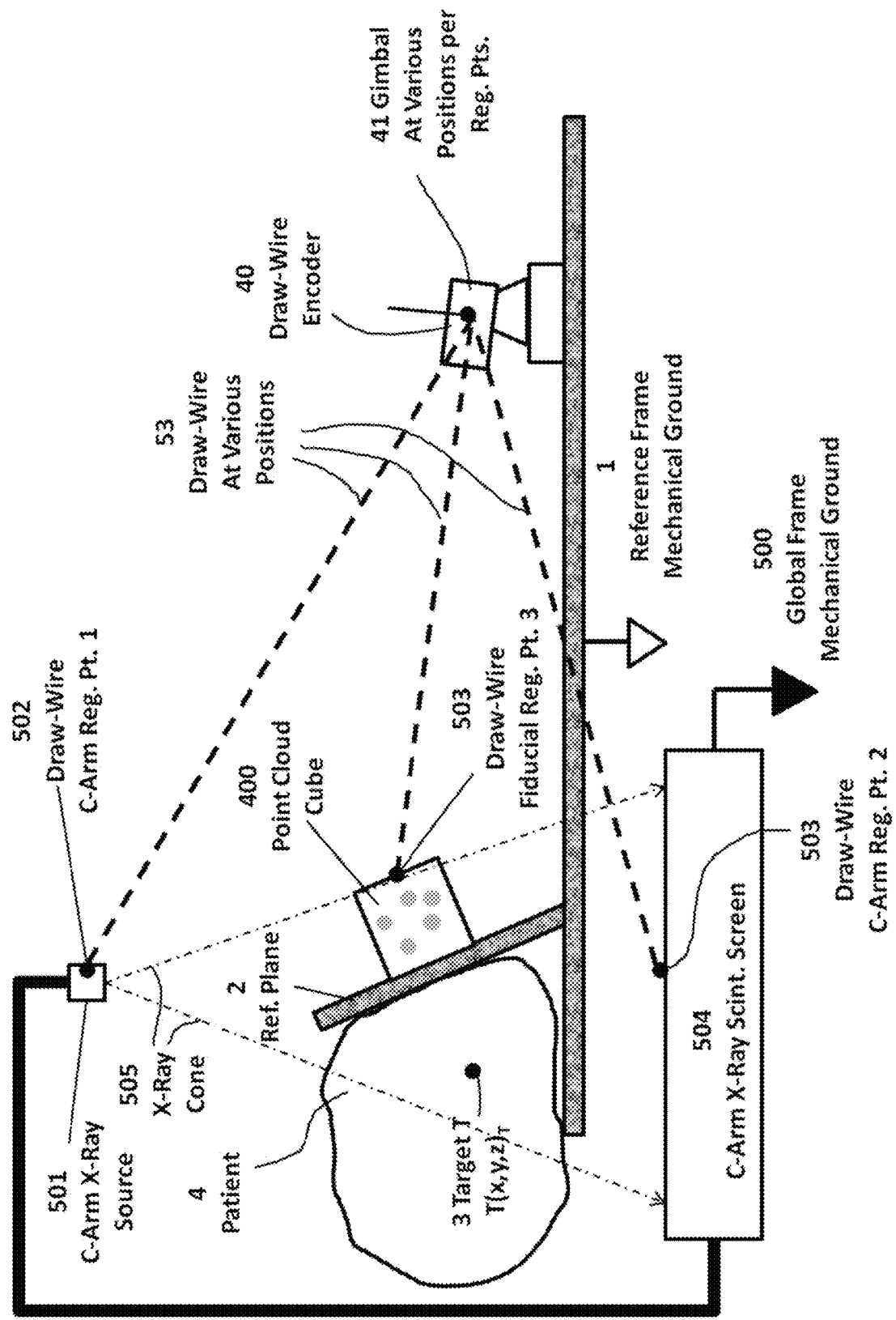
FIG. 9 shows a schematic representation of the 3-dimensional point-cloud fiducial reference system with the present invention and its use to register the spatial coordinate system of the X-ray C-arm and operating room coordinate system.

In FIG. 9, the fiducial cube 400 is resting against a known reference plane 2 and the fiducial cube 400 is completely within the field of view of the X-ray cone 505 produced by the C-arm X-ray source 501. The X-ray cone 505 transects the fiducial cube 400, the patient 4 with desired target point 3, and projects the X-ray image onto the C-arm X-ray scintillation screen 506. The C-arm is anchored to the operating room global frame of reference 500, while the gimbal 41 and reference plane 2 are anchored to a local mechanical reference frame 1. By using the draw-wire 53 and gimbal base 41 to touch various points 502, 503, and 504, the relative positions and orientation of the C-arm, the reference frame mechanical ground 1, global reference frame ground 500, and the patient 4, can all be registered and linked together in a single solid body coordinate system. Note that a minimum of 3 registration touch points are needed at each location 502, 503, and 504 to uniquely establish the 3-dimensional position and orientation of that part. By rotating the C-arm source 501 and scintillation screen 506 together and capturing at minimum, two orthogonal projections, the positions of the fiducial spheres in the point cloud base 400, can be uniquely established via linear algebraic methods as described by Brost et al. (2009).

Figure 10:
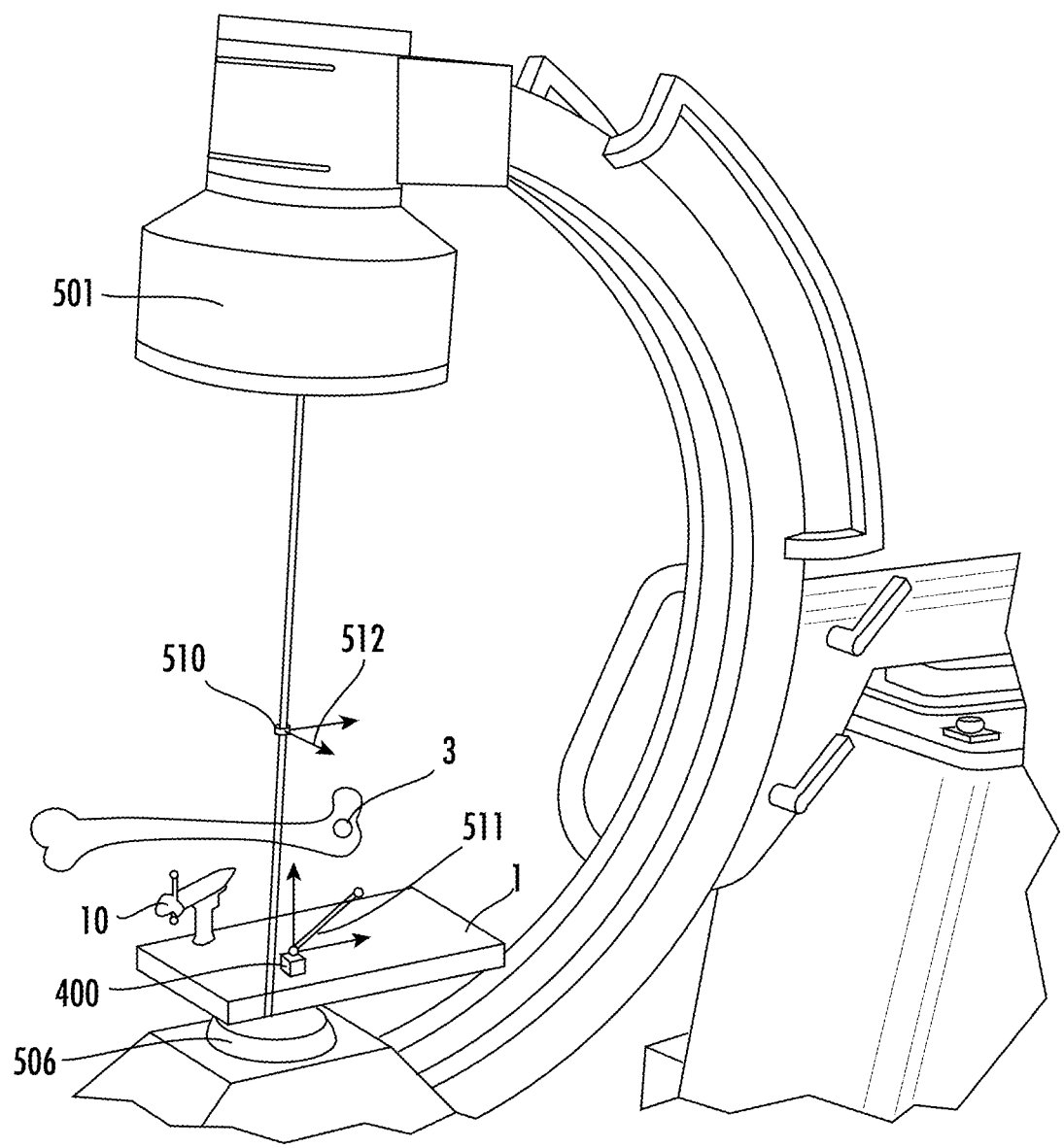
FIG. 10 shows a 3-dimensional perspective view of a C-arm X-ray machine with the present invention and the associated local and global coordinate systems.

FIG. 10 shows an X-ray C-arm system comprised of an X-ray source 501 and X-ray scintillation detector plate 506 with an iso-center 510 and global frame of reference 512, with a 3-dimensional fiducial point-cloud cube 400 with local frame of reference 511. The drill handle 10, target point 3, and reference frame mechanical ground base 1 are also show. As previously stated, the target 3, and the 3-dimensional fiducial 400 must be within the field of view of the X-ray beam path and the scintillation detector screen 506. In order to locate the target 3 which has been selected in the X-ray images, we locate the fiducial 400, which is attached rigidly to the reference frame 1, which is also attached the gimbal 40 (not shown) of the present invention as shown in FIG. 1 but omitted here for visual clarity, and whose position is known in the local coordinate frame 511 of the gimbal 40, in the global coordinate frame of the C-arm 512. The coordinate transform we are looking to calculate is $^{C\text{-}ARM}\xi_{GIMBAL}$.

Note that there is an assumption that the system has been calibrated so that the intrinsic parameters (pixel spacing of the detector, the distance between the X-ray source and detector plane, location of the iso-center of the C-arm) are accurate and extrinsic parameters can be measured with suitable accuracy. To locate a point one needs the intrinsic and extrinsic C-arm camera parameters. As given in (Brost, et al., 2009), the camera model can be taken to be a Pinhole Camera model, with a projection matrix given by:

$$P = K[R|t] \quad (1)$$

The intrinsic parameters K of the X-ray "camera" can be evaluated as:

$$K = [SID\, pox\, SID\, poy\, 1] \quad (2)$$

Where
SID is source to image detector distance
p is the distance between pixels in mm
$o_x$ is the x location of the projected iso-center in pixels on the image
$o_y$ is the y location of the projected iso-center in pixels on the image The Extrinsic Parameters are given by the two rotations $R_\alpha$ and $R_\beta$ and a translation t, where t is the translation from the X-ray source to the iso-center of the C-arm. Note that in (Brost, et al., 2009) the rotation matrix given as $R_\alpha$ is clockwise positive about the Z axis, and $R_\beta$ is clockwise positive about the x-axis. In addition, the axes are aligned with the DICOM patient axes (LPS, X goes from Patient right to patient left, Y goes from patient Anterior to Posterior, and Z goes from Patient Anterior to Superior.)

The rotations are combined into a matrix R given by:

$$R = R_\alpha \cdot R_\beta \quad (3)$$

From equation 1, we can project a global point $w \in R^3$ to $v \in R^3$ where v is a homogenous point in 2d space and w is a homogenous point with 1 as the fourth component. The projection can be written as:

$$v_{\alpha,\beta} = K(R \cdot w + t) \quad (4)$$

To solve for the global C-arm points:

$$w = R^{-1} \cdot (K^{-1} \cdot v_{\alpha,\beta} - t) \quad (5)$$

The 3-dimensional fiducial 400 in C-arm global coordinates 512 can be used to find the translation vector needed to translate the target 3 position into the gimbal 40 frame of reference 511. This is comprised of a translation followed by a rotation to bring the C-arm basis vectors 512 aligned with the gimbal 40 frame of reference basis vectors 511. In this way, multiple angle (>2) projections of the 3-dimensional fiducial are not needed to register the two frames of reference together, as when performing the registration using a multi-angle computed tomographic (CT) reconstruction technique.

There is also disclosed herein a surgical targeting system guided by time of flight sensors strategically mounted on a hand-held or potentially robotic drill, the time of flight sensors being in proximity to x-ray opaque fiducials positioned relative to a subject surgical area located within a defined three dimensional reference frame and wherein the x-ray opaque fiducials are point cloud fiducials using pseudorandom locations used with a deconvolution to establish a global reference XYZ coordinate system in the three dimensional reference frame, and a CPU hardware and software to determine the proximity in space of the associated time of flight sensors as they change course over time.

There is also disclosed herein a surgical targeting system as set forth above, wherein a surgical pathway is determined by a user and includes a drill entry point and an end point and where the drill entry point and the end point are selected by the user and entered into a computer.

There is also disclosed herein a surgical targeting system as set forth above, wherein the receiver is a wideband microphone.

There is also disclosed herein a surgical targeting system as set forth above, wherein the optical time of flight transceiver uses a light emitting diode.

There is also disclosed herein a surgical targeting system as set forth above, wherein the optical time of flight transceiver uses a laser diode.

There is also disclosed herein a surgical targeting system as set forth above, wherein the optical time of flight transceiver uses optical heterodyne modulation to determine the time of flight through an optical phase measurement.

There is also disclosed herein a surgical targeting system as set forth above, wherein the optical time of flight transceiver uses triangulation to determine the distance through optical geometric measurement.

There is also disclosed herein a surgical targeting system as set forth above, wherein further comprising a precision virtual reality system for remote surgery.

There is also disclosed herein a surgical targeting system as set forth above, wherein an offset is used to account for detection of wave inversion.

There is also disclosed herein a surgical targeting system as set forth above, the offset is based on one or more of the wave number, the microphone displacement, and the transmitter or receiver foci.

There is also disclosed herein a three-dimensional aiming system to determine an angle of incline of a terminal workpiece carried by a tool along a workpath from an initial start point to a determined end point and comprising: a two arm linkage which links the terminal workpiece to a fixed point wherein the first arm is an extendable link which can be extended a value n which can be determined and the second arm is a fixed length arm which incorporates the tool, a frame of reference which includes a plurality of senders that define two orthogonal planes and which can be used to establish a set of coordinates for the workpath, a plurality of sensors carried by the tool and in communication with the senders, a CPU having machine readable code to determine the alignment of the terminal workpiece relative to the set of coordinates, and a display that informs the user as to the alignment.

There is also disclosed herein a three-dimensional aiming system as set forth above, wherein the senders and sensors are acoustic or light.

There is also disclosed herein a three-dimensional aiming system as set forth above, further including means to calculate a time of flight determination between the senders and sensors.

There is also disclosed herein a three-dimensional aiming system as set forth above, wherein the optical time of flight sensors use visible to near infrared (400 nm to 800 nm) light to sense the distance from the tool to the reference plane.

There is also disclosed herein a three-dimensional aiming system as set forth above, wherein the senders generate an acoustic signal which is received by the acoustic receivers and a Fast Fourier Transform (FFT) is used by the CPU to extract phase information from the received acoustic signal in order to derive the time of flight.

There is also disclosed herein a three-dimensional aiming system as set forth above, wherein the senders are acoustic transmitters that generate an acoustic pulse signal which is received by the sensors which are acoustic receivers which receive a received pulse signal and a discrete Cross Correlation Function (CCF) between the transmitted acoustic pulse signal and the received pulse signal is used by the CPU to derive the time of flight.

There is also disclosed herein a three-dimensional aiming system as set forth above, wherein the digital signal processing (DSP) is used by the CPU to perform calculations to derive the time of flight.

There is also disclosed herein a three-dimensional aiming system as set forth above, wherein the senders generate both a carrier at a carrier frequency and an acoustic pulse signal which is received by the sensors as a received pulse signal and wherein digital coding schemes are used to modulate the carrier frequency in order to increase a contrast and signal to noise ratios to improve an accuracy of a derivation of the time of flight.

There is also disclosed herein a three-dimensional aiming system as set forth above, wherein the digital coding scheme is a AA55 code.

There is also disclosed herein a three-dimensional aiming system as set forth above, wherein an Octave code scheme having a routine is used to automatically extract a phase reversal or an inflection point for the derivation of the time of flight.

There is also disclosed herein a three-dimensional aiming system as set forth above, further including a video camera to create video images and where the video images are also used simultaneously to aim the terminal workpiece.

There is also disclosed herein a three-dimensional aiming system as set forth above, including the further use of fluoroscopic imaging to derive the tool workpath determined end point.

There is also disclosed herein a three-dimensional aiming system for positional determination and guidance system as set forth above, wherein the accuracy of the guidance of the workpath to the determined end point is at least +/−1 mm.

There is also disclosed herein a three-dimensional aiming system as set forth above, wherein the accuracy of the alignment of the terminal workpiece is at least +/−2 degrees to the set of coordinates.

There is also disclosed herein a hand-held orthopedic instrument which is a drill or wire driver having a three-dimensional aiming system to determine an angle of incline of a terminal workpiece for a surgical tool along a workpath in a patient's body from an initial start point to a determined end point and comprising: a two arm linkage which links the terminal workpiece to a fixed point wherein the first arm is an extendable link which can be extended a value n which can be determined and the second arm is a fixed length arm which incorporates the orthopedic instrument, a frame of reference which includes a plurality of senders that define two orthogonal planes and which can be used to establish a set of coordinates for the workpath, a plurality of sensors carried by the tool and in communication with the senders, a CPU having machine readable code to determine the alignment of the terminal workpiece relative to the set of coordinates, and a display that informs the user as to the alignment.

There is also disclosed herein a hand-held orthopedic instrument which is a drill or wire driver having a three-dimensional aiming system to determine an angle of incline of a terminal workpiece for a surgical tool along a workpath in a patient's body from an initial start point to a determined end point and comprising: a two arm linkage which links the terminal workpiece to a fixed point wherein the first arm is an extendable link which can be extended a value n which can be determined and the second arm is a fixed length arm which incorporates the orthopedic instrument, a frame of reference which includes a plurality of senders that define two orthogonal planes and which can be used to establish a set of coordinates for the workpath, a plurality of sensors carried by the tool and in communication with the senders, a CPU having machine readable code to determine the alignment of the terminal workpiece relative to the set of coordinates, and a haptic feedback member that informs the user as to the alignment.

There is also disclosed herein a method of performing a surgery comprising, the steps of: locating and securing an anatomical area within a three-dimensional reference frame capable of establishing a coordinate system, using x-ray opaque fiducials on the anatomical area to locate points in the coordinate system wherein the x-ray opaque fiducials are point cloud fiducials which use pseudorandom locations with a deconvolution to establish a global reference XYZ coordinate system in the three-dimensional reference frame, using an imaging system to define an endpoint spaced from a starting point within the anatomical area and linking the endpoint to the coordinate system to form a set of desired alignment coordinates, providing a CPU having machine readable code and an instrument having a workpiece, and which bears a sender or receiver which are in communication with a corresponding sender or receiver operable with respect to the reference frame and with the CPU to determine a position of the workpiece in the reference frame, and aligning instrument by hand in the reference frame such that the alignment of the workpiece corresponds to the desired alignment coordinates.

There is also disclosed herein a method of performing a surgery comprising, the steps of: locating and securing an anatomical area within a three-dimensional reference frame capable of establishing a coordinate system, using x-ray opaque fiducials on the anatomical area to locate points in the coordinate system wherein the x-ray opaque fiducials are point cloud fiducials which use pseudorandom locations with a deconvolution to establish a global reference XYZ coordinate system in the three-dimensional reference frame, using an imaging system to define an endpoint spaced from a starting point within the anatomical area and linking the endpoint to the coordinate system to form a set of desired alignment coordinates, providing a CPU having machine readable code and an instrument having a workpiece, and which bears a sender or receiver which are in communication with a corresponding sender or receiver operable with respect to the reference frame and with the CPU to determine a position of the workpiece in the reference frame, and wherein the instrument includes a two arm linkage which links the workpiece to a fixed point at a known location relative to the three-dimensional reference frame and wherein the first arm is an extendable link which can be extended a value n which can be determined and the second arm is a fixed length arm which incorporates the orthopedic instrument, and aligning instrument progressively and over time by hand in the reference frame such that the alignment of the workpiece corresponds to the desired alignment coordinates.

There is also disclosed herein a method of training or performing a surgery by a user of hand-held instrument and comprising, the steps of: locating and securing an anatomical area within a three-dimensional reference frame capable of establishing a coordinate system, using an imaging system to define an endpoint spaced from a starting point within the anatomical area and linking the endpoint to the coordinate system to form a set of desired alignment coordinates, using x-ray opaque fiducials on the anatomical area to locate points in the coordinate system wherein the x-ray opaque fiducials are point cloud fiducials which use pseudorandom locations with a deconvolution to establish a global reference XYZ coordinate system in the three-dimensional reference frame, providing a CPU having machine readable code and the hand-held instrument having a workpiece, and which bears a sender or receiver which are in communication with a corresponding sender or receiver operable with respect to the reference frame and with the CPU to determine a position of the workpiece in the reference frame, and wherein the instrument includes a two arm linkage which links the workpiece to a fixed point at a known location relative to the three-dimensional reference frame and wherein the first arm is an extendable link which can be extended a value n which can be determined and the second arm is a fixed length arm which incorporates the orthopedic instrument, aligning instrument by the hand in the reference frame such that the alignment of the workpiece corresponds to the desired alignment coordinates, and alerting the user as to the location of the instrument relative to the desired alignment coordinates.

There is also disclosed herein a method of performing a hip fixation surgery using a wire driver comprising, the steps of: locating a hip within a three-dimensional reference frame capable of establishing a coordinate system, using an imaging system to define an endpoint in a femoral head of the hip spaced from a starting point on the proximal femur within the hip and linking the endpoint to the coordinate system to form a set of desired alignment coordinates, providing a CPU having machine readable code and a wire driver having a guide wire, and which bears a sender or receiver which are in communication with a corresponding sender or receiver operable with respect to the reference frame and with the CPU to determine a position of the guide wire in the reference frame, aligning the wire driver in the reference frame such that the alignment of the wire corresponds to the desired alignment coordinates, driving the wire using the wire driver, and seating a cannulated screw over the wire driver.

There is also disclosed herein a method of performing a hip fixation surgery as set forth in 48, wherein the wire driver includes a two arm linkage which links the workpiece to a fixed point at a known location relative to the three-dimensional reference frame and wherein the first arm is an extendable link which can be extended a value n which can be determined and the second arm is a fixed length arm which incorporates the orthopedic instrument.

In accordance with the patent statutes, the best mode and preferred embodiment have been set forth; the scope of the invention is not limited thereto, but rather by the scope of the attached claims.

What is claimed is:

1. A positional determination and guidance system to guide the user of a surgical tool having a terminal workpiece over time along a workpath in a patient's body from an initial start point to a determined end point and comprising:
    a base member which has a reference plane and which also supports a two-member robotic arm system comprising of a variable-length proximal arm which is comprised of a flexible and extensible cable-under-tension link fitted with a draw-wire sensor mounted on a 2-axis gimbal fitted with a plurality of angular sensors in a known spatial relationship relative to the initial start point,
    a hand-held tool serving as the second fixed-length distal arm, connected to the proximal arm by means of a 3-axis ball joint, and having a plurality of angular sensors and a plurality of time of flight transceivers for absolute distance to a reference plane,
    a computer processing unit (CPU) having machine readable code to determine positional information of the terminal workpiece along the workpath from the initial start point toward the determined end point, and
    a display that informs the user as to the guidance of the terminal workpiece along the workpath.

2. A positional determination and guidance system as set forth in claim 1, that uses a combination of radio frequency wireless communication and electrical communication via hard-wires between the hand-held tool and the base member.

3. The positional determination and guidance system as set forth in claim 2, including an electronic microprocessor system to calculate a time of flight determination between the transceivers and the reference plane.

4. The positional determination and guidance system as set forth in claim 3, wherein the positional information is provided through the use of angular measurements provided by micro-electro-mechanical systems (MEMS) inertial measurement units (IMUs) used in conjunction with measured and known distances via a forward kinematics equation using a transformation matrix of Denavit-Hartenberg parameters to determine the position and trajectory as a function of time.

5. The positional determination and guidance system as set forth in claim 4, wherein the forward kinematic equations in combination with the time of flight information is used by the CPU to perform calculations to derive the positional information and angular approach.

6. The positional determination and guidance system as set forth in claim 5, wherein the plurality of time of flight transceivers are optical time of flight sensors.

7. The positional determination and guidance system as set forth in claim 3, wherein a combination of forward kinematically derived positions and angles are compared to absolute distances and angles as determined by one of the plurality of time of flight distance transceivers mounted on a distal link.

8. The positional determination and guidance system as set forth in claim 3, wherein the tool handle comprises a distal link.

9. The positional determination and guidance system as set forth in claim 3, wherein the plurality of time of flight transceivers are optical time of flight sensors.

10. The positional determination and guidance system as set forth in claim 1, wherein the transceivers generate light pulses in the visible or near infrared spectrum for use in the guidance of the terminal workpiece.

11. The positional determination and guidance system for a surgical tool path determination as described in claim 1, further including video cameras to create video images and where the video images are used in combination with the data obtained by the angular sensors and the time of flight transceivers.

12. The positional determination and guidance system as set forth in claim 1, including the further use of fluoroscopic imaging to derive the determined end point.

13. The positional determination and guidance system as set forth in claim 1, wherein the accuracy of the guidance of the workpath to the determined end point is at least +/−1 mm.

14. The positional determination and guidance system as set forth in claim 1, wherein the accuracy of the guidance of the workpath to the determined end point is at least +/−2 degrees.

15. The positional determination and guidance system as set forth in claim 1, wherein local and global coordinate systems are spatially registered and calibrated with one another using a combination of a 3-dimensional point-cloud fiducial and the use of a draw-wire touching a 3-dimensional point-cloud fiducial, a C-arm source and scintillation target screen fiducials in order to place their relative (x, y, z) spatial locations relative to one another.

16. The positional determination and guidance system as set forth in claim 1, wherein local and global coordinate systems are spatially registered and calibrated with one another using known intrinsic and extrinsic parameters of a C-arm X-ray camera and the use of two X-ray images taken with a translation and rotation of the C-arm such that global and local frame of reference basis vectors are aligned to permit calculation of the location of a point on a 3-dimensional point-cloud fiducial using linear algebraic equations for ray tracing of a pinhole camera model.

* * * * *